United States Patent [19]

DiGiulio

[11] 3,960,492

[45] June 1, 1976

[54] METHOD FOR DETERMINING AN INDEX OF BINDING PROTEIN CONTENT OF BLOOD

[75] Inventor: Walter DiGiulio, Grosse Pointe Woods, Mich.

[73] Assignee: Nuclear Diagnostics, Inc., Troy, Mich.

[22] Filed: May 31, 1974

[21] Appl. No.: 475,213

[52] U.S. Cl. .............................. 23/230 B; 23/230.3; 252/408; 424/1
[51] Int. Cl.² ..................................... G01N 33/16
[58] Field of Search ..................... 23/230 B; 424/1; 252/408

[56] References Cited
UNITED STATES PATENTS

| | | | |
|---|---|---|---|
| 3,376,114 | 4/1968 | Eberle | 23/230 B |
| 3,451,777 | 6/1969 | DiGiulio | 23/230 B |
| 3,519,390 | 7/1970 | Dickey et al. | 23/230 B |
| 3,646,346 | 2/1972 | Catt | 23/230 B |
| 3,666,854 | 5/1972 | Eisentraut | 23/230 B |
| 3,716,632 | 2/1973 | Fader et al. | 23/230 B |
| 3,730,684 | 5/1973 | Demetriou | 23/230 B |
| 3,743,482 | 7/1973 | Eisentraut | 23/230 B |
| 3,745,211 | 7/1973 | Brown et al. | 23/230 B |
| 3,776,698 | 12/1973 | Eisentraut | 23/230 B |

OTHER PUBLICATIONS

Clark, et al., J. Clin. Endocr. vol. 25, 1965, pp. 39–45.

*Primary Examiner*—R. E. Serwin
*Attorney, Agent, or Firm*—Burton and Parker

[57] ABSTRACT

A method for determining an index of binding proteins in a serum sample comprising the steps of: 1. Forming a mixture of a) the serum sample, having ligand binding sites, b) a quantity (usually a trace amount) of radioactive ligand and c) an amount of non-radioactive ligand such that the total amount of ligand (radioactive and non-radioactive) is in excess of the ligand binding sites available in the serum sample; 2. Contacting the mixture with a quantity of a binder having a preferential affinity for the ligand; and 3. Thereafter determining the distribution of the radioactive ligand such as by measuring the radioactivity of the binder.

The method is particularly applicable for determining thyroxine binding protein content in serum.

The method is also applicable to determine an index of serum free thyroxine as determined by the ratio of the concentration of thyroxine to the concentration of thyroxine binding proteins.

24 Claims, 5 Drawing Figures

METHOD FOR DETERMINING AN INDEX OF BINDING PROTEIN CONTENT OF BLOOD

BACKGROUND

As medicine requires an accurate knowledge of certain constituents of blood, it is desirable to improve various analytical tests to determine the content of various constituents of the blood, such as binding proteins and hormones. Various thyroid hormones are produced in the thyroid gland and are carried in the blood to the body cells where the hormones ultimately produce their well known metabolic effects. The hormones secreted by the thyroid gland include thyroxin, T4, and triiodothyronine, T3. The liver produces proteins such as thyroxin binding globulins (TBG) which are also important in regulating thyroid function.

Upon entering the blood, substantial amounts of T4 and T3 become bound to thyroxine binding proteins, (TBP), in a reversible manner. While the hormones are transported throughout the blood in mostly bound form, clinical studies have shown that it is the concentration of "free" thyroid hormones, e.g. FT4 or FT3 that determines the thyrometabolic status of an individual.

Because of the importance of these various substances, total T4, total T3, free T4, free T3, TBG and other thyroid hormone binding proteins, it is worthwhile to determine their content in the blood.

Various analytical techniques have been proposed. One technique for estimating TBP is an electrophoretic technique which is quite accurate but rather cumbersome for routine clinical medicine.

U.S. Pat. No. 3,451,777 DiGiulio teaches a method and apparatus for determining the thyroid hormone content of blood using a tube, open at the top and bottom, with a resin column therebetween for binding T3.

Nicoloff, et al., *Obstetrics and Gynecology*, Vol. 35, No. 2, February 1970, pages 191-198 teaches the use of a resin sponge technique for estimating TBG values. The method proposed is a modification of the T3 Resin Uptake Test of which U.S. Pat. No. 3,451,777 DiGiulio is an example.

A good summary of related radioimmunoassay (RIA) techniques is given in *Clinical Chemistry*, Vol. 19, No. 2, 1973, pp 145-174.

TBG may also be measured by RIA techniques.

An object of the present invention is to provide a simplified means of measuring binding protein content in blood.

A further object of this invention is to provide a rapid and simple procedure for measuring the TBP level in blood, which can be readily utilized by unskilled technicians in carrying out the method of the invention and in particular for measuring FT4. A further object of the invention is to provide a rapid and simple procedure for measuring antibody levels in blood.

SUMMARY OF THE INVENTION

The invention is concerned with determining an index of binding proteins in a blood sample by forming a mixture of the serum sample having ligand binding sites with a radioactive ligand and an additional amount of ligand so that the total ligand is in excess of the ligand binding sites available in the blood sample; contacting the mixture with a non-specific binder which has a preferential affinity for the ligand and thereafter determining the distribution of radioactive ligand. Preferably the serum sample has antibodies or endogenous binding proteins with binding sites for a ligand.

DESCRIPTIONS OF DRAWINGS

DESCRIPTION OF PREFERRED EMBODIMENTS

Figure 1:
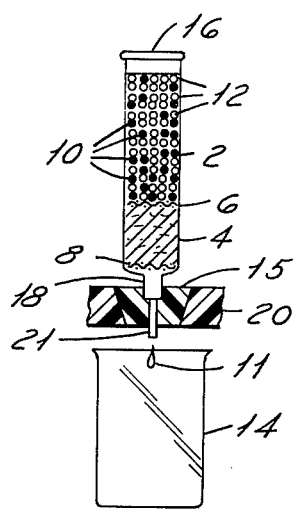
FIG. 1 is a schematic view of the apparatus which may be used in the simplified method of the present invention showing a blood sample in a tube with open top and bottom; the tube sitting in a valve holder, and the blood sample dripping through the valve into a reservoir.

It can be said that the present application is concerned with a method similar to radioimmunoassay techniques and competitive protein binding analysis (CPBA). Generally, the invention is concerned with a method for determining an index of binding proteins in a blood sample comprising the steps of;

1. Forming a mixture of a) the blood sample, having ligand binding sites, b) a quantity of a radioactive ligand and c) an amount of non-radioactive ligand such that the total ligand (radioactive and non-radioactive) is in excess of the ligand binding sites available in the blood sample;

2. Contacting the mixture with a quantity of a binder having a preferential affinity for the ligand; and 3. Thereafter, determining the radioactive distribution of the ligand such as by measuring the radioactivity of the binder.

By a "binding protein" is meant a protein which can bind a ligand to it. By "ligand" is meant a substance which usually is smaller in size than a binding protein and which has an affinity or ability to bind to a binding protein.

While the method is generally applicable to determining concentrations of binding proteins, it is particularly applicable in the preferred embodiment in determining an index of TBP in a blood sample especially TBG. While a blood sample may be employed, it is preferred that plasma or serum, especially serum be used as the sample in forming the mixture prior to contact with the binder.

When one wishes to determine an index of TBP one follows the steps of:

1. Forming a mixture of a) serum having proteins with T4 sites (such as TBG) b) a quantity (usually a trace) of radioactive T4, and c) an additional amount of T4, such that the total amount of T4 is in excess of the binding sites in binding proteins in the sample;

2. Contacting the mixture with a quantity of a non-specific binder having a preferential affinity for T4; and 3. Thereafter determining the radioactive distribution of T4.

Because of the improved technique for determining TBP according to the present invention, it has further been determined that an index of FT4 can likewise be obtained by determining the ratio of total T4 to TBP in the sample comprising the steps:

I. Measuring the total T4 in the sample; and
II. Measuring TBP in the sample by:
 1. Forming a mixture of a) serum having proteins with T4 binding sites such as TBG; b) a quantity of radioactive T4, and c) an additional quantity of T4, such that the total amount of T4 is in excess of the T4 binding sites in the binding proteins of the blood sample;
 2. Contacting the mixture with a quantity of a nonspecific binder having a preferential affinity for T4; and
 3. Thereafter determining the radioactive distribution of T4.

In the above steps, it is indicated that after the ligand contacts the non-specific binder, the radioactive distribution of the ligand is determined. It is to be appreciated that the easier method of determining the radioactive distribution is to measure the radioactivity of the binder after passage of the mixture therethrough. On the other hand, one could also measure the radioactivity of the mixture that has passed through the binder.

Also in the above steps it is indicated that the binder should have a preferential affinity for the ligand. By "affinity" is meant that the binder, although nonspecific, should have the ability to retain or bind or trap or chemically bond or otherwise separate the ligand from the protein bound ligand.

Therefore, it can be said that the binder retains the ligand in preference to the protein bound ligand because the binder has a weak or negligible affinity for binding protein.

It can be said that substantially all of the T4 in blood will be bound to TBP. It is generally believed that the interaction between T4 and TBP can be expressed as an equilibrium between FT4 and bound thyroxin (TBP.T4). This reaction is governed by the law of mass action and can be expressed as:

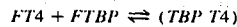

$$FT4 + FTBP \rightleftharpoons (TBP\ T4)$$

Prior to the introduction of the present invention, it was common to determine the amount of unbound or unsaturated sites of TBP because this measurement indirectly reflected hormone content of blood. The tests of the prior art therefore try to determine the unsaturated TBP sites. It would be desirable to measure not just the unsaturated sites but the total amount of TBP, saturated and unsaturated. This can be performed by the present invention. Having a measure of total serum T4 as well as the binding capacity of serum, it is possible to estimate the total concentration of free thyroxin. Free thyroxin is directly proportional to total thyroxin and indirectly proportional to total TBP concentration.

Therefore it can also be stated that the invention can be considered a method of determining an index of free T4 in a blood sample, as the quotient, comprising the steps:
 1. measuring, as the dividend, the total T4 content in a blood sample; and
 2. measuring, as the divisor, the TBP content, or TBG content, of the blood sample.

If an excess of T4 is added to a sample of serum containing TBG, the binding sites in protein are saturated. Excess T4 which cannot bind to the TBG may subsequently be measured by passing the serum sample plus a quantity of radioactive T4 through a nonspecific binder and then measuring the radioactivity of the nonspecific binder.

It is to be appreciated that the most preferred technique is the passing of the mixture through an apparatus shown in FIG. 1. However, satisfactory results may also be obtained if the mixture contacts the binder for a sufficient period of time to allow the excess T4 to bind to the binder. In that situation a swirling action in a test tube or round-bottom vessel would suffice providing the mixture would then be decanted from the vessel, leaving the radioactive T4 and additional T4 bound to the nonspecific binder.

It has been determined that the normal amount of T4 binding capacity of TBG is of the order of twenty micrograms T4 per 100 milliliters of serum. A preferred excess added thyroxin is at least five times the usual amount of binding capacity of TBG and even more preferably about 6.5 times the normal binding capacity of TBG. It is to be appreciated that the sample size plays a role in determining the amount of excess T4 which will be added.

Figure 2:
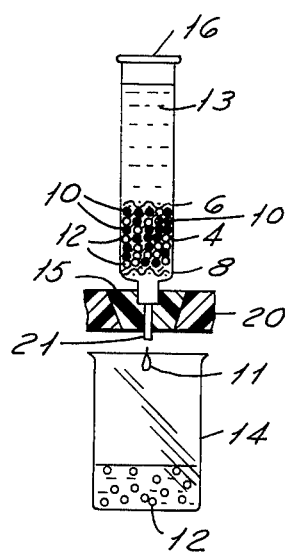
FIG. 2 is a schematic view of the apparatus of FIG. 1 showing the sample as it passes through the test tube where a portion of sample is retained in the tube.
Figure 3:
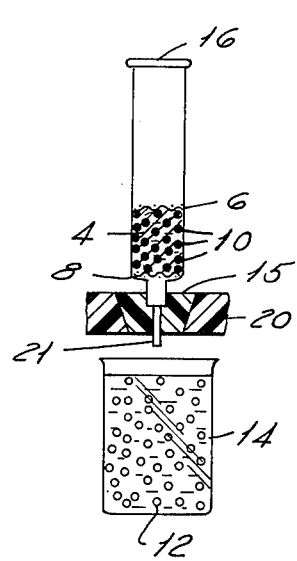
FIG. 3 is a schematic view of the apparatus of FIGS. 1 and 2 after the sample has passed entirely through the test tube.
Figure 5:
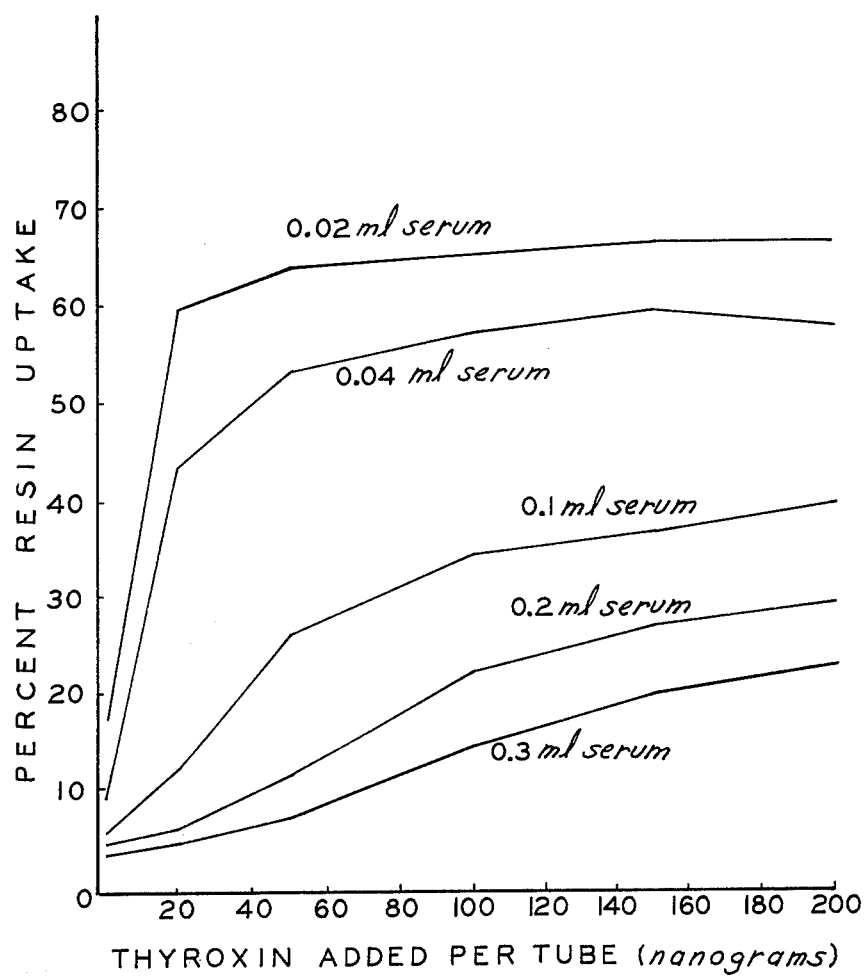
FIG. 5 is a graph showing effect of added exogenous T4 on percent resin uptake.

In determining the amount of excess ligand or T4 employed in a mixture of serum sample, reference is made to FIG. 5. Using the apparatus of FIGS. 1–3, as described below, plotted is the effect of added exogenous thyroxin on percent resin uptake, taking into consideration the variations in sample size. The graph depicts the effects of increasing levels of added T4 on the resin uptake when 0.02 to 0.3 ml% of standard serum (containing 19 m.g.% TBG binding capacity) is added to each assay take. It is noted that after 100 nanograms of T4 has been added, the curves are relatively unresponsive to further changes in T4 concentration. The resin uptake at this point appears to be a function of TBG content only (or the amount of serum added). This curve therefore shows a way for evaluating the TBG content of an unknown sample in reference to a standard curve which is constructed by using varying volumes of a standard serum with known TBG values.

The preferred means of determining the index of TBP is by following the procedures described below; serum is added to the tubular apparatus 2 of FIG. 1 having a nonspecific binder 4 being retained between screens 6 and 8, which binder has an affinity for the T4 in the introduced serum. The serum sample is shown as having free hormone (closed circles 10) and protein-bound hormone (open circles 12).

The mixture 11 of serum, excess T4 and a radioactive T4 passes through valve means 15 into receptacle or reservoir 14. The tubular apparatus 2 is open at the top 16 and at the bottom 18 through which the serum passes as it traverses the nonspecific binder 4. The tubular apparatus 2 fits snugly into the tubular apparatus sample holder 20 via valve means 15 having a valve outlet 21.

As the serum passes through the nonspecific binder, it can be seen that the free hormone (closed circles) is retained by the nonspecific binder while the protein-bound hormone passes into the receptacle 14. After the sample traverses the nonspecific binder the radioactivity is then determined for the free, or nonprotein bound hormone, which has been bound ("trapped") by the binder.

The overall test procedure can be described as follows: First the reagent for the test which contains 0.13 ug thyroxin and approximately 0.1 uCi of I-125 labeled thyroxin/per 4 ml. is dispensed in disposable test tubes (not shown). Aliquotes of 0.1 ml. serum samples are added to these test reagents and are mixed briefly. A standard curve is produced using several volumes of control serum (see FIG. 4). These test mixtures are then poured into columns of nonspecific binder. When all of the liquid has entered the column, the column is washed with 3–5 ml. of distilled water 13 and the activity retained on the column is determined. The time required for the test mixture to traverse the column is approximately 20 seconds. Four or five test procedures can be accomplished simultaneously. The flow rate is accurately controlled by a valve (15 & 21) to which the columns are attached during the procedure.

Figure 4:
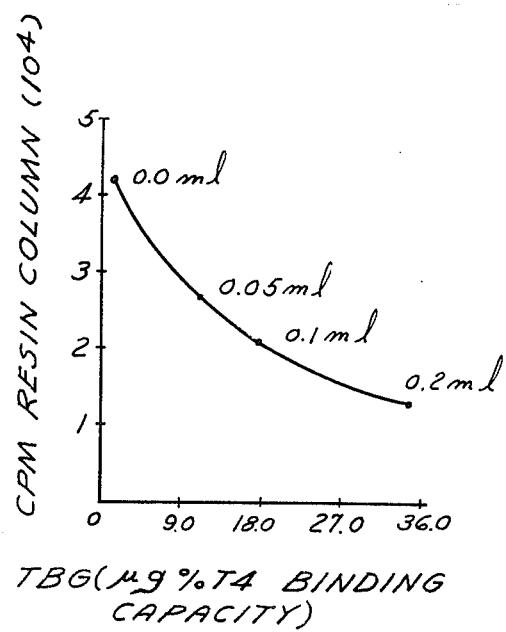
FIG. 4 is a standard curve using standard serum with a known TBG value (e.g. 18 mcg% T4 binding capacity) using various volumes (0.0, 0.05, 0.1 and 0.2 ml) of the standard serum which corresponds to TBG values of 0.0 to 36.0 mcg% T4 binding capacity.

A standard curve is prepared using pooled serum with a known TBG value (18 mcg% T4 binding capacity) so that volumes of 0.0, 0.05, 0.1 and 0.2 ml of pooled serum correspond to TBG values of 0.0 to 36.0 mcg% T4 binding capacity (see FIG. 4). The nonspecific binder radioactivity is determined and converted into TBG (mcg% T4 binding capacity) by reference to the standard curve.

The binding of 125 I-T4 to the binder varies inversely with TBG content of serum. Thus, when the serum TBG concentration is high, a small percentage of labeled thyroxin is "free" to bind to resin columns and vice versa.

Variations in the serum T4 concentration due to hyper or hypothyroidism do not significantly affect the TBG assay since the T4 content of the test reagent is high compared to the endogenous T4 in the assayed serum.

The normal range was established by performing the TBG-CPBA assay on 41 euthyroid healthy hospital employees. The TBG-CPBA value for this group 19.3 ± 3.8 (2 Standard Deviations - SD)mcg% T4 binding capacity. The normal range derived from a larger group of normals (70) which included 29 euthyroid patients with normal T3 resin uptake and T4 tests was 18.9 ± 4.0 (2SD). Twenty-three euthyroid employees or patients taking estrogens or birth control pills had a mean TBG value of 27.2 ± 5.1 (SD) with a range of 19.5 to 39.5. Five of these values fell within the normal range. "Sick" euthyroid patients were selected. The mean TBG value for this group of patients was 15.3 ± 3.0 (SD). The TBG values for 17 hyperthyroid and 17 hypothyroid patients were 16.5 ± 2.9 and 21.0 ± 2.4 respectively.

The correlation coefficient of the above TBG test with the thyroxin binding-globulin binding capacities determined by electrophoretic methods was highly significant, $R=0.97$.

While the above test has been described as a means for determining TBP employing T4, it is to be appreciated that other materials may likewise bind with TBP to achieve the same effect, such as, dilantin and the like using the same procedure of an excess of the appropriate materials.

It should also be pointed out that the aforementioned procedure can be used generally for determining binding proteins, such as TBG, transferrin (an iron binder), ceruloplasmin (protein which binds copper) or in general measure antibodies.

If one wished to determine an index of transferrin, one would form a mixture of serum, a quantity of radioactive iron (e.g. Fe 59) and an excess of iron. The iron would be added as a serum soluble iron salt. With respect to ceruloplasmin, one would add to the serum a quantity of radioactive copper and an excess of copper, again as a serum soluble salt.

In the aforementioned discussion of various studies, the nonspecific binder that was employed was a resin material called Dowex 1 × 8, 20–50 mesh (manufactured by Dow Chemical which is a strongly basic anion exchange resin and is based upon trimethyl benzyl ammonium, cross linked with divinyl benzene). Other nonspecific binders may also be employed such as Amberlite IRA 400 CL 20—5 mesh, chloride form, manufactured by Rohm and Hass, Philadelphia, Pa. It should also be appreciated that the nonspecific binder that would be employed would depend upon the binding protein which one wishes to determine. Other suitable examples of nonspecific binders are various gels, such as, polyacrylamides, sephadex (trademark for cross linked dextrans), various absorption and adsorption mediums such as charcoal, powdered cellulose, micro fine particles of silica, glass beads of controlled pore size, diatomaceous earth, and the like.

It has also been determined that the reagent or solution into which the serum sample is placed prior to passing through the nonspecific binder may have other components therein for decreasing the binding effect of other proteins. For example, it has been found desirable to include a barbital buffer which inhibits or retards other proteins, such as, thyroxine binding prealbumin (TBPA) so they will not bind to the TBG.

The barbital buffer is preferably 0.21M barbital buffer having a ph of 8.6 which is obtained by adding 2.74 grams acid diethyl barbital and 15.4 grams sodium diethyl barbiturate in deionized water to 1 liter volume.

Other components may likewise be added to the reagent or solution into which the serum is placed, such as, various bacteriostatic or anti-fungal agents. These materials are added in an amount to give effective anti-bacterial or anti-fungal activity, preferably no higher than 1% by weight, even more preferably 0.01 to 0.5% by weight. Suitable materials are sodium azide in the amount of 0.1%, merthiolate (trademark for thiomerosal) and the like. It should be appreciated that these anti-bacterial or anti-fungal agents that may be employed are only those that do not interfere with the binding proteins in the serum.

What is claimed is:
1. A method for determining an index of binding proteins in a blood sample comprising the steps of:
   1. Forming a mixture of a) the blood sample, having ligand binding sites, b) a known quantity of a radioactive ligand and c) a known amount of nonradioactive ligand wherein the total amount of the ligand is in excess of the ligand binding sites available in the blood sample;
   2. Contacting the mixture with a quantity of a binder having a preferential affinity for the ligand; and
   3. Thereafter, determining the radioactive distribution of the ligand.

2. The method of claim 1 wherein the blood sample is serum.

3. The method of claim 2 wherein the radioactivity of the ligand is determined by measuring the radioactivity of the binder.

4. The method of claim 2 wherein the binder is a resin having an affinity for the ligand.

5. The method of claim 2 wherein the binder is retained in a tube having an open top and bottom portion, whereby the mixture may pass therethrough in a rapid manner.

6. The method of claim 5 wherein the mixture passes through the resin column in a period of time less than one minute.

7. The method of claim 2 wherein the amount of binder employed substantially exceeds the amount of radioactive material added to the mixture.

8. A method for determining an index of thyroxine binding protein in a blood sample comprising the steps of:
1. Forming the mixture of a) the blood sample having proteins which have ligand binding sites, b) a known quantity of a radioactive ligand and c) a known amount of nonradioactive ligand wherein the total amount of the ligand is in excess of the ligand binding sites in the blood sample;
2. Contacting the mixture with a quantity of a binder having a preferential affinity for the ligand; and
3. Thereafter, determining the radioactive distribution of the ligand.

9. The method of claim 8 wherein the blood sample is serum.

10. The method of claim 9 wherein the ligand is T4.

11. The method of claim 10 wherein the total amount of nonradioactive and radioactive T4 added to the mixture is at least 5 times the available ligand binding sites of the binding protein.

12. The method of claim 8 wherein the TBP is TBG.

13. The method of claim 9 wherein the binder is a resin having an affinity for the ligand.

14. The method of claim 9 wherein the binder is retained in a tube having an open top and bottom portion whereby the solution may be passed therethrough in a rapid manner.

15. The method of claim 14 wherein the time for passing the mixture through the binder is less than one minute.

16. The method of claim 9 wherein the mixture further comprises a barbital buffer.

17. The method of claim 9 wherein the mixture further comprises an effective anti-fungal amount of an anti-fungal agent.

18. The method of claim 9 wherein the mixture further comprises an effective anti-bacterial amount of an anti-bacterial agent.

19. A method of determining an index of free T4 by determining the ratio of total T4 to thyroxine binding protein in a blood sample, comprising the steps of:
1. Measuring the total T4 content in the blood sample; and
2. Measuring thyroxine binding protein in the sample by:
   A. Forming a mixture of (i) the blood sample having thyroxine binding protein and T4 binding sites, (ii) a known quantity of radioactive T4 and (iii) a known amount of nonradioactive T4 wherein the total amount of T4 added is in excess of the ligand binding sites in the thyroxine binding protein;
   B. Contacting the mixture with a quantity of a binder having an affinity for the T4; and
   C. Thereafter determining the radioactive distribution of the added T4 and thereby determine the content of thyroxine binding protein in the sample.

20. The method of claim 19 wherein the sample is serum.

21. A method for determining an index of free T4 in a blood sample, as the quotient, comprising the steps:
1. Measuring as the dividend the total T4 content in a blood sample; and
2. Measuring as the divisor the thyroxine binding protein content of the blood sample.

22. A method for determining an index of thyroxine binding globulin in a blood sample comprising the steps of:
1. Forming a mixture of a) the blood sample having said globulin which has ligand binding sites, b) a known quantity of a radioactive ligand, and c) a known amount of nonradioactive ligand wherein the total amount of the ligand is in excess of the ligand binding sites in the blood sample;
2. Contacting the mixture with a quantity of a binder having a preferential affinity for the ligand; and
3. Thereafter, determining the radioactive distribution of the ligand.

23. The method of claim 22 wherein the blood sample is serum.

24. The method of claim 22 wherein the ligand is T4 and the total amount of nonradioactive and radioactive T4 added to the mixture is at least 5 times the available ligand binding sites of thyroxine binding globulin.

* * * * *